(12) United States Patent
Hanschen et al.

(10) Patent No.: US 8,973,225 B2
(45) Date of Patent: Mar. 10, 2015

(54) STRUCTURED SURFACE WITH MULTIPLE-POST CAPS AND METHOD OF MAKING THE SAME

(75) Inventors: Thomas P. Hanschen, Mendota Heights, MN (US); Ronald W. Ausen, St. Paul, MN (US); William J. Kopecky, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 308 days.

(21) Appl. No.: 12/974,640

(22) Filed: Dec. 21, 2010

(65) Prior Publication Data

US 2012/0151720 A1 Jun. 21, 2012

(51) Int. Cl.
*A44B 18/00* (2006.01)
*B29C 67/00* (2006.01)

(52) U.S. Cl.
CPC ......... *B29C 67/0044* (2013.01); *A44B 18/0065* (2013.01)
USPC .............................. 24/452; 24/444; 428/100

(58) Field of Classification Search
CPC ........... A44B 18/0003; A44B 18/0007; A44B 18/00015; A44B 18/0019; A44B 18/0061; A44B 18/0065; A44B 18/00; A44B 18/0046; A44B 18/0049; A44B 18/0053
USPC .............................. 24/452, 442, 446; 428/100
See application file for complete search history.

(56) References Cited

U.S. PATENT DOCUMENTS

| | | | |
|---|---|---|---|
| 3,192,589 A | 7/1965 | Pearson | |
| 4,775,310 A | 10/1988 | Fischer | |
| 4,839,131 A | 6/1989 | Cloeren | |
| 4,894,060 A | 1/1990 | Nestegard | |
| 5,077,870 A | 1/1992 | Melbye et al. | |
| 5,212,853 A | 5/1993 | Kaneko | |
| 5,460,769 A * | 10/1995 | Kaneko | 264/318 |
| 5,537,723 A | 7/1996 | Yoshida et al. | |
| 5,664,302 A * | 9/1997 | Thomas | 24/452 |
| 5,679,302 A | 10/1997 | Miller et al. | |

(Continued)

FOREIGN PATENT DOCUMENTS

| | | |
|---|---|---|
| EP | 0 619 085 | 10/1994 |
| EP | 1 774 866 | 4/2007 |

(Continued)

OTHER PUBLICATIONS

International Search Report of PCT/US2011/066136, dated Aug. 28, 2013, 9 pages.

(Continued)

*Primary Examiner* — Jack W Lavinder

(57) ABSTRACT

A structured surface, which includes a thermoplastic backing sheet and a first upstanding element, is disclosed. The first upstanding element includes multiple, spaced-apart posts and a single cap at the distal ends of the multiple, spaced-apart posts. The structured surface furthermore typically includes a plurality of spaced-apart, upstanding posts with caps on their distal ends, where the ratio of the caps to the posts is less than one-to-one. Also disclosed is a method of making a structured surface. The method includes providing a thermoplastic backing sheet with a plurality of spaced-apart, upstanding posts; and deforming the distal ends to form caps on at least some of the spaced-apart, upstanding posts. At least some of the caps upon forming touch at least one adjacent cap to form a conjoined cap at the distal ends of multiple posts.

20 Claims, 1 Drawing Sheet

(56) References Cited

U.S. PATENT DOCUMENTS

| | | | |
|---|---|---|---|
| 5,749,129 A | 5/1998 | Murasaki et al. |
| 5,845,375 A | 12/1998 | Miller et al. |
| 5,868,987 A | 2/1999 | Kampfer et al. |
| 5,913,482 A | 6/1999 | Akeno |
| 5,953,797 A | 9/1999 | Provost et al. |
| 6,000,106 A | 12/1999 | Kampfer et al. |
| 6,039,911 A | 3/2000 | Miller et al. |
| 6,054,091 A | 4/2000 | Miller et al. |
| 6,106,922 A | 8/2000 | Cejka et al. |
| 6,132,660 A | 10/2000 | Kampfer |
| 6,190,594 B1 | 2/2001 | Gorman et al. |
| 6,368,097 B1 | 4/2002 | Miller et al. |
| 6,544,245 B2 | 4/2003 | Neeb et al. |
| 6,558,602 B1 | 5/2003 | Melbye et al. |
| 6,708,378 B2 | 3/2004 | Parellada et al. |
| 6,767,492 B2 | 7/2004 | Norquist et al. |
| 6,814,912 B2 | 11/2004 | Ausen et al. |
| 6,899,841 B2 | 5/2005 | Buzzell et al. |
| 7,052,636 B2 | 5/2006 | Ausen et al. |
| 7,214,334 B2 | 5/2007 | Jens et al. |
| 7,275,290 B2 | 10/2007 | Clarner et al. |
| 7,828,545 B2 * | 11/2010 | Duffy ............................ 425/542 |
| 7,897,078 B2 | 3/2011 | Petersen et al. |
| 2003/0145440 A1 | 8/2003 | Ausen et al. |
| 2003/0182776 A1 | 10/2003 | Ausen et al. |
| 2004/0031130 A1 | 2/2004 | Clarner et al. |
| 2004/0187276 A1 | 9/2004 | Seth et al. |
| 2005/0132544 A1 | 6/2005 | Seth et al. |
| 2005/0271858 A1 | 12/2005 | Ausen et al. |
| 2008/0018025 A1 | 1/2008 | Duffy |
| 2011/0147475 A1 | 6/2011 | Biegler et al. |
| 2011/0151171 A1 | 6/2011 | Biegler et al. |
| 2012/0151722 A1 | 6/2012 | Hertlein et al. |

FOREIGN PATENT DOCUMENTS

| | | |
|---|---|---|
| EP | 2179671 | 4/2010 |
| JP | 09-121908 | 5/1997 |
| WO | WO 03/101238 | 12/2003 |
| WO | WO 2010/050831 | 5/2010 |
| WO | WO 2011/163193 | 12/2011 |

OTHER PUBLICATIONS

Supplementary European Search Report for EP 1185 2097, dated Nov. 27, 2014.

* cited by examiner

STRUCTURED SURFACE WITH MULTIPLE-POST CAPS AND METHOD OF MAKING THE SAME

BACKGROUND

Articles with one or more structured surfaces are useful in a variety of applications (e.g., abrasive discs, assembly of automobile parts, and disposable absorbent articles). The articles may be provided as films that exhibit, for example, increased surface area, mechanical fastening structures, or optical properties.

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Mechanical fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

The hooks of hook and loop fastening systems may be formed with a curved shape or they may be substantially upright stems that are deformed to include, for example, a head in the shape of mushroom. Some methods, which have varying degrees of versatility and complexity, are available to control the shape of loop-engaging heads. See, e.g., U.S. Pat. Nos. 3,192,589 (Pearson); 5,953,797 (Provost et al.); 6,132,660 (Kampfer); 6,558,602 (Melbye et al.) and 6,708,378 (Parellada et al.).

SUMMARY

The present disclosure provides, in some aspects, a structured surface with a plurality of upstanding, capped posts on a thermoplastic backing. For at least some of the capped posts, more than one post supports a single cap. Thus, among the capped posts of the structured surface disclosed herein, the ratio of the caps to the posts is less than one-to-one. The structured surfaces may be useful, for example, because of their different modes of disengagement from a loop material when compared to a conventional fastener having a single cap on a single post. The present disclosure further provides methods of making such structured surfaces, one of which includes deforming the distal ends of multiple posts to provide a single, conjoined cap supported by multiple posts.

In one aspect, the present disclosure provides a structured surface including a thermoplastic backing sheet and a first upstanding element. The first upstanding element includes multiple, spaced-apart posts having proximal and distal ends, with the proximal ends attached to the thermoplastic backing sheet; and a single cap at the distal ends of the multiple, spaced-apart posts.

In another aspect, the present disclosure provides a structured surface including a thermoplastic backing sheet and a plurality of spaced-apart, upstanding posts. The spaced-apart, upstanding posts have proximal and distal ends, with the proximal ends attached to the thermoplastic backing sheet and with caps on the distal ends. The ratio of the caps to the posts is less than one-to-one.

In another aspect, the present disclosure provides a method of making a structured surface. The method includes:
providing a thermoplastic backing sheet with a plurality of spaced-apart, upstanding posts having proximal and distal ends, with the proximal ends attached to the thermoplastic backing sheet; and
deforming the distal ends to form caps on at least some of the spaced-apart, upstanding posts, wherein at least some of the caps upon forming touch at least one adjacent cap to form a conjoined cap at the distal ends of multiple posts.

In some embodiments of the foregoing aspects, the structured surface may be a mechanical fastener, for example. In these embodiments, the upstanding elements are fastening elements.

The structured surfaces (e.g., mechanical fasteners) according to the present disclosure may overcome common modes of loop disengagement from male fastening elements. Such failure modes include cap flexing and post bending, both of which represent failures associated with the male fastening elements. Single caps at the distal ends of multiple posts typically will be effectively larger than individual caps on single posts. The larger effective caps can be more resistant to cap flexing. Having multiple posts support a single cap also typically increases the effective post thickness, which reduces the likelihood of the post bending mode of failure. Advantageously, increasing the effective post thickness using multiple, spaced-apart posts can reduce the likelihood of post bending without increasing the amount of material required to make the capped posts. The multiple-post caps disclosed herein may alter the shear and peel characteristics of the structured surfaces disclosed herein.

The structured surfaces (e.g., mechanical fasteners) according to and/or made according to the present disclosure can also provide caps having a large size but having short, thin cap overhangs, which may be desirable, for example, for loop engagement. The single caps (e.g., conjoined caps) disclosed herein can have irregular shapes, which may be patterned and aligned for directional peel and shear performance. For example, multiple posts aligned in the machine direction that support a single cap may provide enhanced machine-direction shear performance.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The term "structured surface" refers to a surface with other than a planar or smooth surface.

The term "upstanding" refers to posts that protrude from the thermoplastic backing and includes posts that stand perpendicular to the backing and posts that are at an angle to the backing other than 90 degrees.

The terms "multiple" and "plurality" both refer to more than one (e.g., at least two). As used herein, the term "multiple posts" is typically used in connection with single or conjoined caps at the distal ends of more than one post (e.g., in first upstanding elements). As used herein, the term "plurality of posts" is typically used in connection with a population of posts that includes of combination of those having single caps on single posts and those having single caps on multiple posts.

The term "spaced-apart" refers to posts that are formed to have a distance between them. "Spaced-apart" posts do not touch each other even when they collectively support a single cap.

Caps upon forming that are said to be "shaped at least partially by at least one adjacent cap" are those that have a shape that is influenced by the at least one adjacent cap as described below.

Distal caps that are "separable" by stretching refers to distal caps that are not fused together.

The terms "first" and "second" are used in this disclosure in their relative sense only. It will be understood that, unless otherwise noted, those terms are used merely as a matter of convenience in the description of one or more of the embodiments.

The term "loop-engaging" as used herein relates to the ability of a mechanical fastener element (i.e., hook element) to be mechanically attached to a loop material. Generally, hook elements with loop-engaging heads have a cap shape that is different from the shape of the post. The loop-engageability of hook elements may be determined and defined by using standard woven, nonwoven, or knit materials. A region of posts with loop-engaging caps generally will provide, in combination with a loop material, at least one of a higher peel strength, higher dynamic shear strength, or higher dynamic friction than a region of posts without loop-engaging caps.

The term "machine direction" (MD) as used herein denotes the direction of a running, continuous web of the thermoplastic useful for some embodiments of the method of making a structured surface disclosed herein. When a patch of a structured surface is a smaller portion cut from a continuous web, the machine direction generally corresponds to the length "L" of the structured surface. As used herein, the terms machine direction and longitudinal direction are typically used interchangeably. The term "cross-direction" (CD) as used herein denotes the direction which is essentially perpendicular to the machine direction. When a patch of a structured surface is a smaller portion cut from a continuous web, the cross direction corresponds to the width "W" of the structured surface.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
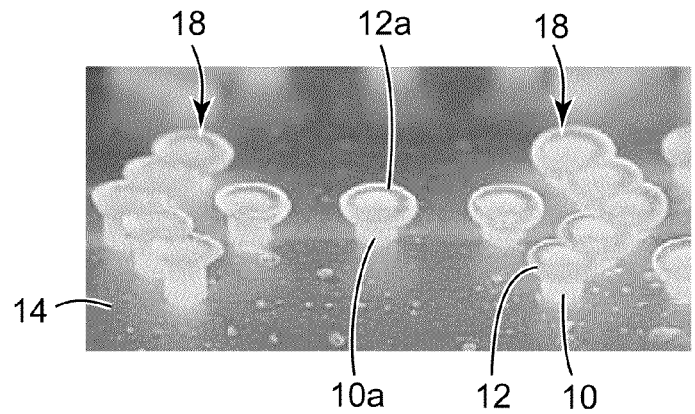
FIG. 1 is a photograph of a perspective view of an exemplary embodiment of a structured surface according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 2:
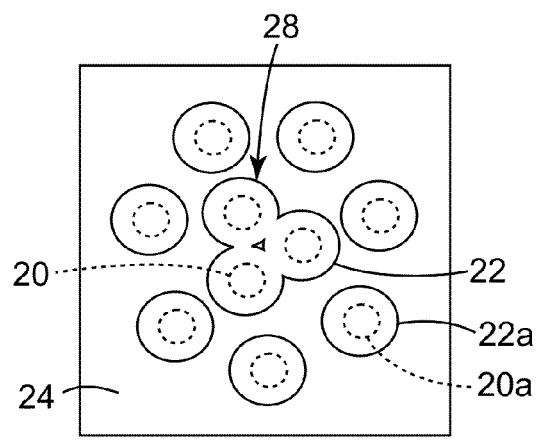
FIG. 2 is a top view of another embodiment of a structured surface according to the present disclosure.
Figure 3:
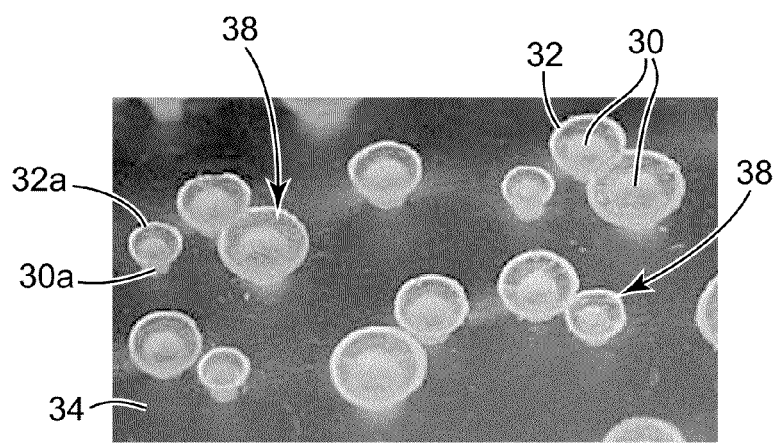
FIG. 3 is a photograph of a perspective view of yet another embodiment of a structured surface according to the present disclosure.

FIGS. 1 to 3 illustrate exemplary structured surfaces (e.g., mechanical fasteners) according to the present disclosure. In each of FIGS. 1 to 3, the structured surface includes a thermoplastic backing sheet 14, 24, and 34 and first upstanding elements 18, 28, and 38. The first upstanding elements 18, 28, and 38 have multiple, spaced-apart posts 10 and 30 (not shown in the top view of FIG. 2). The spaced-apart posts of first upstanding elements 18, 28, and 38 have proximal and distal ends, with the proximal ends attached to the thermoplastic backing sheet 14, 24, and 34. The first upstanding elements 18, 28, and 38 have a single cap 12, 22, and 32 on the distal ends of the multiple, spaced-apart posts 10 and 30 (not shown in FIG. 2). In each of the illustrated embodiments, the structured surface further includes a second upstanding element which has a single post 10a, 20a, 30a having a proximal and distal end. The proximal end of the single post 10a, 20a, 30a is attached to the thermoplastic backing sheet 14, 24, and 34, and there is a distal cap 12a, 22a, and 32a (that is, a single distal cap) on the distal end of each post 10a, 20a, and 30a. In the structured surfaces disclosed herein, there may be any number of first upstanding elements and optionally any number of second upstanding elements on the thermoplastic backing sheet. As shown in FIGS. 1 to 3, there is a plurality of spaced-apart, upstanding posts 10, 10a; 20a; and 30, 30a having proximal and distal ends, with the proximal ends attached to the thermoplastic backing sheet 14, 24, and 34. There are caps 12, 12a; 22, 22a; and 32, 32a on the distal ends of the spaced-apart, upstanding posts 10, 10a; 20a; and 30, 30a, and the ratio of caps 12, 12a; 22, 22a; and 32, 32a to posts 10, 10a; 20a; and 30, 30a, is less than one-to-one. In some embodiments, the number of caps divided by the number of posts is up to 0.9, 0.8, 0.7, 0.6, 0.5, or 0.4. The caps 12, 12a, 22, 22a, 32, and 32a typically have a loop-engaging shape.

In some embodiments, including the embodiments illustrated in FIGS. 1 and 2, the first upstanding element 18 and 28 comprises at least three spaced-apart posts 10 (not visible in FIG. 2). In FIG. 2, the first upstanding element 28 has three spaced-apart posts that are not visible in the top view shown in FIG. 2. In FIG. 1, the first upstanding element 18 has five spaced-apart posts 10. Advantageously, the structured surface (e.g., mechanical fastener) may be designed to have first upstanding elements with any desired number of (e.g., 2, 3, 4, 5, 6, or more) spaced-apart posts. In some embodiments, including the embodiment illustrated in FIG. 3, the first upstanding element 38 has two spaced-apart posts 30.

As shown in FIGS. 1 to 3, the structure surface (e.g., mechanical fastener) may be designed to have a variety of desirable configurations with the first upstanding elements 18, 28, and 38 having a variety of desirable shapes. The single cap typically has a different shape than the cross-sectional shape of the posts. In FIG. 1, first upstanding elements 18 and single caps 12 are in the shape of "V's", which are separated from each other on the thermoplastic backing 14 and point in different (e.g., opposing) directions. The single cap 12 has a perimeter with at least one segment of concavity; in the illustrated embodiment there are multiple segments of concavity within each "V" shape. The second upstanding elements, made up of single post 10a and distal cap 12a, are arranged in rows extending between two first upstanding elements. In FIG. 2, first upstanding elements 28 and single cap 22 have a three-lobed shape. The single cap 22 has a perimeter with at least one segment of concavity; in the illustrated embodiment, there are three segments of concavity, one where each pair of lobes meet. In FIG. 2, the single cap 22 also has a through-hole in the center of the three lobes. The through-hole is an opening in the cap that can provide a pathway, however small, to the thermoplastic backing 24. The second upstanding elements, made up of single post 20a and distal cap 22a, are arranged in a ring around first upstanding element 28. In FIG. 3, the first upstanding elements 38 and single caps 32 have a two-lobed shape, which resembles a pair of intersecting circles. The upstanding elements 38 are oriented in different directions. The single cap 32 has a perimeter with at least one segment of concavity; in the illustrated embodiment, there are two segments of concavity where the lobes meet, one on each side of the cap 32. The second upstanding elements, made up of single post 30a and distal cap 32a, are arranged randomly among first upstanding elements 38. The presence of concavity provides the possibility of multiple, different convex shapes within a single cap. This can be advantageous, for example, for providing an irregular shape for enhanced loop engagement.

In the illustrated embodiments, at least a portion of the multiple, spaced-apart posts are not uniformly spaced on the thermoplastic backing. For example, in FIG. 1, the multiple, spaced-apart posts 10 are in groups of five, wherein the five multiple, spaced-apart posts 10 are spaced close to each other within a first upstanding element 18 but farther away from another group of five multiple, spaced-apart posts 10 in another first upstanding element 18. Similarly, in FIG. 3, the multiple, spaced-apart posts are in groups of two, wherein the two multiple, spaced-apart posts are spaced close to each other within a first upstanding element 38 but farther away from another group of two multiple, spaced-apart posts in another first upstanding element 38.

Furthermore, the multiple, spaced-apart posts in the first upstanding elements 18, 28, and 38 and the single posts 10a, 20a, and 30a in the second upstanding elements are not uniformly spaced. For example, in FIG. 1 the multiple, spaced-apart posts 10 in the arrow-shaped first upstanding elements 18 are spaced more closely together than the single posts 10a in the second upstanding elements. In the embodiment illustrated in FIG. 2 the multiple, spaced-apart posts in the multi-lobed-shaped first upstanding elements 28 are spaced more closely together than the single posts (not shown) in the second upstanding elements. Similarly, in the embodiment illustrated in FIG. 3 the multiple, spaced-apart posts in the first upstanding elements 38 are spaced more closely together than the single posts 30a in the second upstanding elements.

In some embodiments, the multiple, spaced-apart posts have different cross-sectional areas. For example, in the embodiment illustrated in FIG. 3, within a first upstanding element 38, the multiple, spaced-apart posts 30 have different cross-sectional areas. Furthermore, the multiple, spaced-apart posts 30 have different maximum width dimensions (i.e., diameters). Also, among different first upstanding elements 38, the cross-sectional areas and maximum width dimensions of the posts 30 need not be the same. In some embodiments, at least one of the multiple-spaced apart posts has a different cross-sectional area from the single post of the second upstanding element. Furthermore, at least one of the multiple-spaced apart posts has a different maximum width dimension (i.e., diameter) from the single post of the second upstanding element. Referring again to FIG. 3, the cross-sectional area and maximum width dimension (i.e., diameter) in at least one of the spaced-apart posts 30 in a first upstanding element can be different from the cross-sectional area and maximum width dimension of the single post 30a in the second upstanding element. The cross-sectional areas and maximum width dimensions of the single posts 30a may also differ from one another.

Many thermoplastic materials are useful for structured surfaces (e.g., mechanical fasteners) according to and/or made according to the present disclosure. Suitable thermoplastic materials for the thermoplastic backing sheet 14, 24, and 34 with multiple, spaced-apart upstanding posts 10 and 30 and optionally single posts 10a, 20a, and 30a include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; poly(acrylonitrile -butadiene-styrene); plasticized polyvinylchlorides; and mixtures thereof. Typically, the thermoplastic is a polyolefin (e.g., polyethylene, polypropylene, polybutylene, ethylene copolymers, propylene copolymers, butylene copolymers, and copolymers and blends of these materials). The various thermoplastic materials described above can be formulated into a master batch having a desired property (e.g., color).

In some embodiments, the thermoplastic backing sheet 14, 24, and 34 with multiple, spaced-apart posts 10 and 30 and optionally single posts 10a, 20a, and 30a can be made from a multilayer or multi-component melt stream of thermoplastic materials. This can result in posts formed at least partially from a different thermoplastic material than the one predominately forming the backing. Various configurations of upstanding posts made from a multilayer melt stream are shown in U.S. Pat. No. 6,106,922 (Cejka et al.), for example. A multilayer or multi-component melt stream can be formed by any conventional method. A multilayer melt stream can be formed by a multilayer feedblock, such as that shown in U.S. Pat. No. 4,839,131 (Cloeren). A multicomponent melt stream having domains or regions with different components could also be used. Useful multicomponent melt streams could be formed by use of inclusion co-extrusion die or other known methods (e.g., that shown in U.S. Pat. No. 6,767,492 (Norquist et al.).

In the structured surfaces (e.g., mechanical fasteners) according to and/or made according to the present disclosure, the thermoplastic backing sheet 14, 24, and 34 and the multiple, spaced-apart posts 10, 20, and 30 or plurality of spaced-apart, upstanding posts 10, 10a, 20a, 30, and 30a are typically integral (that is, formed at the same time as a unit, unitary). The thermoplastic backing is typically in the form of a sheet, film, or web that may have an essentially uniform thickness with the spaced-apart upstanding posts directly attached to the thermoplastic backing. The thermoplastic backing sheet typically is in the form of a continuous film, wherein "continuous" refers to having no holes in the film. Upstanding posts on a backing sheet can be made, for example, by conventional extrusion through a die and cast molding techniques. In some embodiments, a thermoplastic material is fed onto a continuously moving mold surface with cavities having the inverse shape of the upstanding posts. The thermoplastic material can be passed between a nip formed by two rolls or a nip between a die face and roll surface, with at least one of the rolls having the cavities (i.e., at least one of the rolls is a tool roll). Pressure provided by the nip forces the resin into the cavities. In some embodiments, a vacuum can be used to evacuate the cavities for easier filling of the cavities. The nip is typically sufficiently wide such that a continuous backing is formed over the cavities. The mold surface and cavities can optionally be air or water cooled before stripping the integrally formed backing and upstanding posts from the mold surface such as by a stripper roll.

Suitable tool rolls can be made, for example, by drilling (e.g., by electron beam) a series of holes having the inverse shape of the multiple, spaced-apart posts 10, 20, and 30 into the cylindrical face of a metal mold or sleeve. Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). The exposed surface of the mold, sleeve, plate, or wire may be coated to impart surface properties such as increased wear resistance, controlled release characteristics, and controlled surface roughness. The coating, if present, is preferably selected so that the adhesion of the thermoplastic material to the tool roll is less than the cohesion of the thermoplastic material at the time of the removal of the thermoplastic backing from the tool roll.

Another exemplary method for forming a thermoplastic backing sheet 14, 24, and 34 with multiple, spaced-apart posts 10, 20, and 30 or a plurality of spaced-apart, upstanding posts 10, 10a, 20a, 30, and 30a includes using a flexible mold belt defining an array of upstanding post-shaped cavities as described in U.S. Pat. No. 7,214,334 (Jens et al.). The mold belt is trained about first and second rolls, and a source of molten thermoplastic material is arranged to deliver the thermoplastic to the mold belt. The apparatus is constructed to force the plastic resin into the upstanding post-shaped cavities of the belt under pressure in a gap to mold the array of upstanding posts while forming the thermoplastic web layer.

In addition to the continuous methods described above, it is also envisioned that thermoplastic backing sheets having spaced-apart posts can be prepared using batch processes (e.g., single piece injection molding). The thermoplastic backing sheet may have any suitable dimension, but length and width dimensions of at least 10 cm may be useful.

In the structured surface (e.g., mechanical fastener) according to and/or made according to the present disclosure, the spaced-apart posts 10, 10a, 20, 30, and 30a, which may be made, for example, by any of the methods described above, may have a variety of cross-sectional shapes. For example, the cross-sectional shape of the post may be a polygon (e.g., square, rectangle, hexagon, pentagon, or cross), which may be a regular polygon or not, or the cross-sectional shape of the post may be curved (e.g., round or elliptical).

In the structured surface or mechanical fastener according to and/or made according to the present disclosure, the thermoplastic backing sheet 14, 24, and 34 may have a variety of thicknesses. For example, the thickness of the thermoplastic backing sheet may be up to about 750, 500, 400, 250, or 150 micrometers, depending on the desired application. In some embodiments, the thickness of the backing is at least about 5, 10, 30, 50, 75, or 100 micrometers, depending on the desired application. In some embodiments, the thickness of the thermoplastic backing sheet is in a range from 10 to about 225 micrometers, from about 30 to about 200 micrometers, or from about 50 to about 150 micrometers. The thermoplastic backing sheet may have an essentially uniform cross-section, or the thermoplastic backing sheet may have additional structure (e.g., grooves) beyond what is provided by the upstanding posts which may be imparted, for example, by at least one of the forming rolls described above. However, in some embodiments, the thermoplastic backing sheet has a smooth surface aside from the upstanding posts (e.g., in first and second upstanding elements). In some embodiments, the thermoplastic backing sheet is essentially flat.

In some embodiments, spaced-apart posts, upon being formed on a backing, for example, by any of the methods described above, have a maximum height (above the backing) of up to 3 millimeters (mm), 1.5 mm, 1 mm, or 0.5 mm and, in some embodiments a minimum height of at least 0.05 mm, 0.075 mm, 0.1 mm, or 0.2 mm. In some embodiments, the posts have aspect ratio (that is, a ratio of height over a width dimension) of at least about 2:1, 3:1, or 4:1. The aspect ratio may be, in some embodiments, up to 10:1. The posts may have a cross-section with a maximum width dimension of up to 1 (in some embodiments, up to 0.75, 0.5, or 0.45) mm. In some embodiments, the posts have a cross-section with a width dimension between 10 μm and 350 μm. As described above, the cross-sectional dimensions among different posts can be different. In some embodiments, the maximum width dimension of some posts may be up to twice the maximum width dimension of other posts. The term "width dimension" should be understood to include the diameter of a post with a circular cross-section. When the post has more than one width dimension (e.g., in a rectangular or elliptical cross-section shaped post), the aspect ratio described herein is the height over the largest width dimension.

In the structured surface or mechanical fastener according to and/or prepared according to the present disclosure, the spaced-apart posts, which may be made, for example, by any of the methods described above, may have a shape that tapers, for example, from the proximal end to the distal end. The base portion may have a larger width dimension than the distal tip, which may facilitate the removal of the post from the mold surface in the methods described above.

It should be understood that "multiple, spaced-apart posts" do not include ribs that can be useful precursors to mechanical fastening elements (e.g., elongate ribs that are profile extruded and subsequently cut to form hook elements upon stretching in the direction of the ribs). Such ribs would also not be considered "loop-engaging" because they would not be able to engage loops before they are cut and stretched. In some embodiments, methods according to the present disclosure do not include cutting ribs.

A number of methods may be useful for making the caps in the structured surface according to the present disclosure. In some embodiments, material from the upstanding posts is used to make the caps, for example, by deforming the caps.

In some embodiments, the method of making a mechanical fastener disclosed herein comprises providing a thermoplastic backing sheet with a plurality of spaced-apart, upstanding posts having proximal and distal ends, with the proximal ends attached to the thermoplastic backing sheet; and deforming the distal ends to form caps on at least some of the spaced-apart, upstanding posts, wherein at least some of the caps upon forming touch at least one adjacent cap to form a conjoined cap at the distal ends of multiple posts. In these embodiments, the distal ends of multiple posts provide the material for the conjoined cap. The level of deformation depends, for example, on the temperature used during the deformation and the length of time the deformation is carried out. In some embodiments, the level of deformation is high enough that the edges of the distal caps touch and do not allow further flow into a circular shape. As a result, the at least some caps upon forming are shaped at least partially by the at least one adjacent distal cap. That is, the material in the distal caps flows into available open spaces to form cap shapes that are determined by the height and spacing of the posts. In some embodiments, the level of deformation is high enough such that no distinct pattern of individual caps is visible in the conjoined cap. The caps formed after the distal ends of the posts are deformed, including the conjoined caps, are considered to have a loop-engaging shape.

The density of the spaced-apart posts in the method of making a structured surface is among the factors that influences whether at least some caps upon forming touch at least one adjacent cap after deforming the distal ends of the posts to provide capped posts. The posts need to be spaced close enough so that at least some caps can touch upon deformation. The height of the posts (described above) and the level of deformation, which depends, for example, on temperature and time, also influence whether at least some caps upon forming touch at least one adjacent cap. Methods for deforming the distal tips to provide capped posts are now described in detail.

A variety of methods are useful for deforming the distal tips of the spaced-apart posts. The caps 12, 12a, 22, 22a, 32, and 32a that are formed after the deformation are larger in area than the cross-sectional area of the bases of the posts attached to the thermoplastic backing, and at least some of the caps touch at least one other cap. A ratio of a width dimension of the formed cap to the post measured at the base is typically at least 1.5:1 or 3:1 and may be up to 5:1 or greater. The capped posts are typically shorter than the posts before deformation. In some embodiments, the capped posts have a height (above the backing) of at least 0.025 mm, 0.05 mm, or 0.1 mm and, in some embodiments, up to 2 mm, 1.5 mm, 1 mm, or 0.5 mm.

In some embodiments of the method of making a structured surface according to the present disclosure, deforming the distal ends to form caps 12, 12a, 22, 22a, 32, and 32a comprises heating the distal ends. Typically, a combination of heat and pressure is used to deform the distal ends of the posts to form caps. The heat and pressure can be applied sequentially or simultaneously.

In some embodiments, deforming comprises contacting the distal ends with a heated surface. The heated surface may be a flat surface or a textured surface such as that disclosed in 6,708,378 (Parellada et al.) or U.S. Pat. No. 5,868,987 (Kampfer et al.). In some embodiments, wherein the thermoplastic backing 14, 24, and 34 with spaced-apart posts is a web of indefinite length, the deforming comprises moving the web in a first direction through a nip having a heated surface member and an opposing surface member such that the heated surface member contacts the distal tips. In these embodiments, the heated surface may be, for example, a capping roll. In some embodiments, the surfaces used to contact the distal ends may not be heated. In these embodiments, the deformation is carried out with pressure and without heating.

In some embodiments, the heated surface may be a heated roll opposite a curved support surface forming a variable nip having a variable nip length as described, for example, in U.S. Pat. No. 6,368,097 (Miller et al.). The curved support surface may curve in the direction of the heated roll, and the heated roll may include a feeding mechanism for feeding the thermoplastic backing with spaced-apart posts through the variable nip to compressively engage the web between the heated roll and the support surface.

In embodiments wherein deforming comprises heating the distal ends of the spaced-apart posts, including any of the embodiments described above, the heating is typically carried out below a melt temperature of the distal ends. When the thermoplastic material used to form the upstanding posts is a copolymer (e.g., copolymers of ethylene and propylene), the distal ends may have more than one melt temperature. In these embodiments, "below a melt temperature of the distal ends" means below at least one of the melt temperatures. However, in some embodiments, the heating is carried out above the melt temperature of the distal ends. In embodiments where the thermoplastic material used to form the upstanding posts is a copolymer with multiple melt temperatures, "above a melt temperature of the distal ends" means above at least one of the (e.g., typically the highest) melt temperatures.

In some embodiments of the structured surface according to the present disclosure, the thermoplastic backing sheet has stretch-induced molecular orientation in at least one direction. Likewise, in some embodiments of the method of making a structured surface according to the present disclosure, the method includes stretching the thermoplastic backing sheet 14, 24, and 34 in at least one direction. Stretching can be carried out on a web biaxially or monoaxially. Biaxial stretching means stretching in two different directions in the plane of the thermoplastic backing sheet 14, 24, and 34. Typically, but not always, in a continuous web, the two different directions are the machine direction and the cross-direction. Biaxial stretching can be performed sequentially by stretching the thermoplastic backing sheet, for example, first in one of the two directions and subsequently in the other of the two directions. Biaxial stretching can also be performed essentially simultaneously in both directions. Monoaxial stretching refers to stretching in only one direction in the plane of the thermoplastic backing 14, 24, and 34. Typically, monoaxial stretching is performed in one of the machine direction or cross direction but other stretch directions are also possible. In some embodiments wherein the thermoplastic backing is stretched, it may be useful, for example, to stretch in a direction perpendicular to a direction in which at least some of the multiple posts supporting a single cap are aligned.

When the thermoplastic backing sheet is a web of indefinite length, for example, monoaxial stretching in the machine direction can be performed by propelling the thermoplastic web over rolls of increasing speed. The most versatile stretching method that allows for monoaxial, sequential biaxial, and simultaneous biaxial stretching of a thermoplastic web employs a flat film tenter apparatus. Such an apparatus grasps the thermoplastic web using a plurality of clips, grippers, or other film edge-grasping means along opposing edges of the thermoplastic web in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. Monoaxial and biaxial stretching can be accomplished, for example, by the methods and apparatus disclosed in U.S. Pat. Appl. Pub. No. 2005/0202205 (Petersen et al.) and the references cited therein. Flat film tenter stretching apparatuses are commercially available, for example, from Brückner Maschinenbau GmbH, Siegsdorf, Germany.

For any of the embodiments of structured surface (e.g., mechanical fastener) or the methods of making a structured surface described herein, the structured surface may be in the form of a roll, from which patches of the structured material (e.g., mechanical fastening patches), for example, may be cut in a size appropriate to the desired application. In this application, the thermoplastic backing sheet 14, 24, and 34 may also be a patch that has been cut to a desired size. In some of these embodiments, the second surface of the thermoplastic backing sheet (i.e., the surface opposite the first surface from which the spaced-apart posts project) may be coated with an adhesive (e.g., a pressure sensitive adhesive). In such embodiments, when the structured surface is in the form of a roll, a release liner may be applied to the exposed adhesive.

In some embodiments of the structured surfaces and methods of making them disclosed herein, the thermoplastic backing sheet 14, 24, and 34 is not joined to a carrier, at least when it is initially formed. In other embodiments, the method of making a structured surface further comprises joining a second surface of the thermoplastic backing sheet (i.e., the surface opposite the first surface from which the spaced-apart posts project) to a carrier. The thermoplastic backing sheet may be joined to a carrier, for example, by lamination (e.g., extrusion lamination), adhesives (e.g., pressure sensitive adhesives), or other bonding methods (e.g., ultrasonic bonding, compression bonding, or surface bonding). Such joining methods may be carried out before deforming the distal tips of the upstanding posts or after deforming the distal tips of the upstanding posts, as desired. The thermoplastic backing sheet may be joined to a carrier during the formation of the thermoplastic backing sheet with upstanding posts. The resulting article may be a fastening laminate, for example, a fastening tab joined to the backsheet of an absorbent article useful for joining the front waist region and the rear waist region of an absorbent article.

The carrier, which in some embodiments may be joined to the second surface of the thermoplastic backing sheet, may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). The term "nonwoven" when referring to a carrier or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

One or more zones of the carrier may comprise one or more elastically extensible materials extending in at least one direction when a force is applied and returning to approximately their original dimension after the force is removed. The term "elastic" refers to any material that exhibits recovery from stretching or deformation. Likewise, "nonelastic" materials, which do not exhibit recovery from stretching or deformation, may be useful for the carrier as well.

The fastening laminate that can be formed after joining the thermoplastic backing to a carrier may be useful, for example, in absorbent articles. Exemplary absorbent articles have at least a front waist region, a rear waist region, and a longitudinal center line bisecting the front waist region and the rear waist region, wherein at least one of the front waist region or the rear waist region comprises the structured surface made according to the method disclosed herein. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article. The fastening laminate may also be useful, for example, for disposable articles such as sanitary napkins. A sanitary napkin typically includes a back sheet that is intended to be placed adjacent to the wearer's undergarment. The back sheet may comprise a thermoplastic backing with spaced-apart, upstanding capped posts to securely attach the sanitary napkin to the undergarment, which mechanically engages with the capped posts.

The longitudinal direction "L" (in some embodiments, the machine direction) of the structured surface may be generally aligned with the longitudinal center line of the absorbent article. In embodiments wherein the first upstanding elements comprise angles, the angles are aligned at a nonzero angle to the longitudinal center line of the absorbent article, which may enhance the peel performance of the structured surface when the fastening tab is removed from a mating surface on the absorbent article. The nonzero angle may be in a range from 30 to 90 degrees, 50 to 90 degrees, 60 to 90 degrees, 75 to 90 degrees, 80 to 90 degrees, or 85 to 90 degrees.

In some embodiments where the carrier is a fibrous web, joining the second surface of the thermoplastic backing sheet to a carrier comprises impinging heated gaseous fluid (e.g., ambient air, dehumidified air, nitrogen, an inert gas, or other gas mixture) onto a first surface of the fibrous web while it is moving; impinging heated fluid onto the second surface of the backing sheet while the continuous web is moving, wherein the second surface is opposite the first surface of the backing sheet; and contacting the first surface of the fibrous web with the second surface of the backing sheet so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing sheet may be carried out sequentially or simultaneously. The term "surface-bonded" when referring to the bonding of fibrous materials means that parts of fiber surfaces of at least portions of fibers are melt-bonded to the second surface of the backing sheet, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary sheet to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto. Methods and apparatus for joining a continuous thermoplastic web to a fibrous carrier web using heated gaseous fluid may be found in co-pending U.S. patent applications with Ser. Nos. 61/288,952 and 61/288,959, both filed Dec. 22, 2009, and incorporated herein by reference in their entirety.

Selected Embodiments of the Disclosure

In a first embodiment, the present disclosure provides a structured surface comprising a thermoplastic backing sheet and a first upstanding element, the first upstanding element comprising:

multiple, spaced-apart posts having proximal and distal ends, with the proximal ends attached to the thermoplastic backing sheet; and a single cap at the distal ends of the multiple, spaced-apart posts.

In a second embodiment, the present disclosure provides a structured surface according to the first embodiment, wherein at least a portion of the multiple, spaced-apart posts are not uniformly spaced on the thermoplastic backing sheet.

In a third embodiment, the present disclosure provides a structured surface according to the first or second embodiment, further comprising a second upstanding element comprising a single post having a proximal and distal end, with the proximal end attached to the thermoplastic backing sheet and one cap on the distal end of the single post.

In a fourth embodiment, the present disclosure provides a structured surface according to any one of the first to third embodiments, wherein at least one of the multiple-spaced apart posts has a different cross-sectional area from the single post of the second upstanding element.

In a fifth embodiment, the present disclosure provides a structured surface according to any one of the first to fourth embodiments, wherein the multiple, spaced-apart posts have different cross-sectional areas from each other.

In a sixth embodiment, the present disclosure provides a structured surface according to any one of the first to fifth embodiments, wherein the first upstanding element comprises at least three spaced-apart posts.

In a seventh embodiment, the present disclosure provides a structured surface according to the sixth embodiment, wherein the single cap has a perimeter with at least one segment of concavity.

In an eighth embodiment, the present disclosure provides a structured surface according to the sixth embodiment, wherein the single cap comprises a through-hole.

In a ninth embodiment, the present disclosure provides a structured surface according to any one of the first to eighth embodiments, wherein the single cap has a multi-lobed shape.

In a tenth embodiment, the present disclosure provides a structured surface according to any one of the first to ninth embodiments, wherein the structured surface is a mechanical fastener.

In an eleventh embodiment, the present disclosure provides a structured surface according to any one of the first to tenth embodiments, wherein the thermoplastic backing sheet is a web of indefinite length.

In a twelfth embodiment, the present disclosure provides a structured surface according to the eleventh embodiment, wherein the web is wound into a roll.

In a thirteenth embodiment, the present disclosure provides a structured surface comprising:

a thermoplastic backing sheet; and a plurality of spaced-apart, upstanding posts having proximal and distal ends, with the proximal ends attached to the thermoplastic backing sheet and with caps on the distal ends, wherein a ratio of the caps to the posts with caps on the distal ends is less than one-to-one.

In a fourteenth embodiment, the present disclosure provides a structured surface according to the thirteenth embodiment, wherein at least a portion of the plurality of spaced-apart, upstanding posts is not uniformly spaced on the thermoplastic backing.

In a fifteenth embodiment, the present disclosure provides a structured surface according to the thirteenth or fourteenth embodiment, wherein at least some of the posts of the plurality of spaced-apart, upstanding posts have different cross-sectional areas.

In a sixteenth embodiment, the present disclosure provides a structured surface according to any one of the thirteenth to fifteenth embodiments, wherein at least some of the caps are at the distal ends of at least three spaced-apart posts.

In a seventeenth embodiment, the present disclosure provides a structured surface according to the sixteenth embodiment, wherein at least some of the caps have a perimeter with at least one segment of concavity.

In an eighteenth embodiment, the present disclosure provides a structured surface according to the sixteenth embodiment, wherein at least some of the caps comprise a through-hole.

In a nineteenth embodiment, the present disclosure provides a structured surface according to any one of the thirteenth to eighteenth embodiments, wherein at least some of the caps have a multi-lobed shape.

In a twentieth embodiment, the present disclosure provides a structured surface according to any one of the thirteenth to nineteenth embodiments, wherein the structured surface is a mechanical fastener.

In a twenty-first embodiment, the present disclosure provides a structured surface according to any one of the thirteenth to twentieth embodiments, wherein the thermoplastic backing sheet is a web of indefinite length.

In a twenty-second embodiment, the present disclosure provides a structured surface according to the twenty-first embodiment, wherein the web is wound into a roll.

In a twenty-third embodiment, the present disclosure provides a method of making a structured surface, the method comprising:

providing a thermoplastic backing sheet with a plurality of spaced-apart, upstanding posts having proximal and distal ends, with the proximal ends attached to the thermoplastic backing sheet; and deforming the distal ends to form caps on at least some of the spaced-apart, upstanding posts, wherein at least some of the caps upon forming touch at least one adjacent cap to form a conjoined cap at the distal ends of multiple posts.

In a twenty-fourth embodiment, the present disclosure provides a method according to the twenty-third embodiment, wherein the at least some caps upon forming are shaped at least partially by the at least one adjacent cap.

In a twenty-fifth embodiment, the present disclosure provides a method according to the twenty-third or twenty-fourth embodiment, wherein at least a portion of the plurality of spaced-apart, upstanding posts are not uniformly spaced on the thermoplastic backing sheet.

In a twenty-sixth embodiment, the present disclosure provides a method according to any one of the twenty-third to twenty-fifth embodiments, wherein at least some of the caps upon forming do not touch at least one adjacent cap.

In a twenty-seventh embodiment, the present disclosure provides a method according to any one of the twenty-third to twenty-sixth embodiments, wherein the conjoined cap has at least three posts.

In a twenty-eighth embodiment, the present disclosure provides a method according to the twenty-seventh embodiment, wherein the conjoined cap has a perimeter with at least one segment of concavity.

In a twenty-ninth embodiment, the present disclosure provides a method according to the twenty-seventh embodiment, wherein the conjoined cap comprises a through-hole.

In a thirtieth embodiment, the present disclosure provides a method according to any one of the twenty-third to twenty-ninth embodiments, wherein the conjoined cap has a multi-lobed shape.

In a thirty-first embodiment, the present disclosure provides a method according to any one of the twenty-third to thirtieth embodiments, wherein at least some of the posts in the plurality of spaced-apart, upstanding posts have at least one of different cross-sectional areas or different shapes.

In a thirty-second embodiment, the present disclosure provides a method according to any one of the twenty-third to thirty-first embodiments, wherein the thermoplastic backing sheet is a web of indefinite length.

In a thirty-third embodiment, the present disclosure provides a method according to the thirty-second embodiment, wherein the web is wound into a roll.

In a thirty-fourth embodiment, the present disclosure provides a method according to any one of the twenty-third to thirty-third embodiments, wherein the structured surface is a mechanical fastener.

Embodiments of the present disclosure are further illustrated by the following example, but the particular materials and amounts thereof recited in these examples, as well as other conditions and details, should not be construed to unduly limit this disclosure.

EXAMPLE

A film press, (Wabash MPI, Wabash, Ind.), was used to form posts on a thermoplastic backing sheet. The platens were preheated to 350° F. A sandwich was then made up for pressing consisting of 2 smooth steel plates approximately 0.125 inch thick, 2 sheets of 4 mil PET film, a piece of polypropylene film approximately 10 mils thick, and a pattern plate 20 mils thick with laser-drilled holes for posts. For the structured surface shown in the photograph of FIG. 1, the holes had diameters of a nominal 250 microns. For the structured surface shown in the photograph of FIG. 3, the holes had diameters nominally of 165, 244, and 320 microns.

The sandwich was put together as follows: steel sheet, PET film, pattern plate, polypropylene film, PET film, steel sheet. The sample sandwich was placed between the platens at low pressure to warm up the sandwich plates. Then the sample was pressed at approximately 10 tons to press the polypropylene into the pattern plate. The sample was cooled with a cold platen. Then the polypropylene posts were capped using a household iron with wax paper. The iron was set to "wool". The wax paper was set on top of the stems to be capped. The iron was set on top of the wax paper and stems for approximately 5 seconds.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A structured surface comprising:
   a thermoplastic backing sheet;
   multiple, spaced-apart posts having proximal and distal ends, wherein the proximal ends directly attached to the thermoplastic backing sheet, and wherein at least some of the multiple, spaced-apart posts are not uniformly spaced on the thermoplastic backing sheet; and
   a first upstanding male fastening element comprising:
      at least two of the multiple, spaced-apart posts having proximal and distal ends, with the proximal ends directly attached to the thermoplastic backing sheet; and
      a single cap at the distal ends of the at least two of the multiple, spared-apart posts.

2. A structured surface according to claim 1 further comprising a second upstanding male fastening element comprising a single post of the multiple, spaced-apart posts with one cap on the distal end of the single post.

3. A structured surface according to claim 2, wherein at least one of the multiple-spaced apart posts of the first upstanding male fastening element has a different cross-sectional area from the single post of the second upstanding male fastening element.

4. A structured surface according to claim 1, wherein the multiple, spaced-apart posts of the first upstanding male fastening element have different cross-sectional areas.

5. A structured surface according to claim 1, wherein the single cap has a perimeter with at least one segment of concavity, or wherein the single cap comprises a through hole.

6. A structured surface according to claim 1, wherein the single cap has a multi-lobed shape.

7. A structured surface according to claim 1, wherein the thermoplastic backing sheet is a web.

8. A structured surface according to claim 7, wherein the web is wound into a roll.

9. A structured surface comprising:
   a thermoplastic backing sheet having no holes; and a plurality of male fastening elements with posts having proximal and distal ends, with the proximal ends directly attached to the thermoplastic backing sheet and with caps on the distal ends, wherein at least some of the male fastening elements comprise at least three spaced-apart posts and a single cap at the distal ends of the at least three spaced-apart posts.

10. A structured surface comprising:

a thermoplastic backing sheet; and a plurality of spaced-apart upstanding posts having proximal and distal ends, with the proximal ends attached directly to the thermoplastic backing sheet and with caps on the distal ends, wherein at least some of the spaced-apart, upstanding posts are not uniformly spaced on the thermoplastic backing, and wherein for at least some of upstanding posts with caps, more than one post supports a single cap.

11. A structured surface according to claim 10, wherein the structured surface is a mechanical fastener.

12. A method of making a structured surface, the method comprising:

providing a thermoplastic backing sheet with a plurality of spaced-apart, upstanding posts having proximal and distal ends, wherein the proximal ends are directly attached to the thermoplastic backing sheet, and wherein at least a portion of the plurality of spaced-apart, upstanding posts is not uniformly spaced on the thermoplastic backing sheet: and deforming the distal ends to form caps on at least some of the spaced-apart, upstanding posts, wherein at least some of the caps upon forming touch at least one adjacent cap to form a conjoined cap at the distal ends of multiple posts.

13. A method according to claim 12, wherein the at least some caps upon forming are shaped at least partially by the at least one adjacent cap.

14. A method according to claim 12, wherein at least some of the caps upon forming do not touch at least one adjacent cap.

15. A method according to claim 12, wherein the conjoined cap has at least three posts.

16. A method according to claim 12, wherein the cojoined cap has a perimeter with at least one segment of concavity, or wherein the conjoined cap comprises a through-hole.

17. A method according to claim 16, wherein the conjoined cap has a multi-lobed shape.

18. A method according to claim 12, wherein at least some of the posts in the plurality of spaced-apart, upstanding posts have at least one of different shapes or different cross-sectional areas.

19. A structured surface comprising:

a thermoplastic backing sheet, having no holes; and a plurality of male fastening elements with posts having proximal and distal ends, with the proximal ends directly attached to the thermoplastic backing sheet and with caps on the distal ends, wherein at least some of the male fastening elements comprise at least two spaced-apart posts and a single cap at the distal ends of at least two spaced-apart posts.

20. A structured surface according to claim 19, wherein at least some of the caps have a perimeter with at least one segment of concavity, or wherein at least some of the caps comprise a through-hole.

* * * * *